United States Patent
Godfrey

(10) Patent No.: US 6,652,277 B1
(45) Date of Patent: Nov. 25, 2003

(54) DENTIST'S MATRIX CONTACT INSTRUMENT

(76) Inventor: Duane Kent Godfrey, 3255 Western Ave., Idaho Falls, ID (US) 83406

( * ) Notice: Subject to any disclaimer, the term of this patent is extended or adjusted under 35 U.S.C. 154(b) by 67 days.

(21) Appl. No.: 10/082,896

(22) Filed: Feb. 26, 2002

(51) Int. Cl.$^7$ ................................................ A61C 3/14
(52) U.S. Cl. ...................... 433/159; 433/153; 81/302; 81/355
(58) Field of Search ............................... 433/159, 160, 433/39, 3, 4, 153, 154, 155, 158; 81/302, 355

(56) References Cited

U.S. PATENT DOCUMENTS

| | | | |
|---|---|---|---|
| 1,806,339 A | * | 5/1931 | Ferris et al. ............... 81/302 |
| 2,027,470 A | * | 1/1936 | Caruso ....................... 433/158 |
| 3,377,705 A | * | 4/1968 | Tofflemire ................. 433/155 |
| 3,623,227 A | * | 11/1971 | Tofflemire ................. 433/160 |
| 4,669,979 A | * | 6/1987 | Snead ........................... 433/4 |
| 5,257,558 A | * | 11/1993 | Frazin-Nia et al. ......... 433/159 |

* cited by examiner

Primary Examiner—John J. Wilson
(74) Attorney, Agent, or Firm—Robert A. deGroot

(57) ABSTRACT

A hand operated dentist's instrument having two adjacent tines that spread apart when the instrument handles are squeezed. The tines are used to press against a matrix band surrounding a molar and press the matrix band and adjacent teeth away from a central molar being repaired. The handles are spring-load to return to an open-handle and closed-tine position.

6 Claims, 3 Drawing Sheets

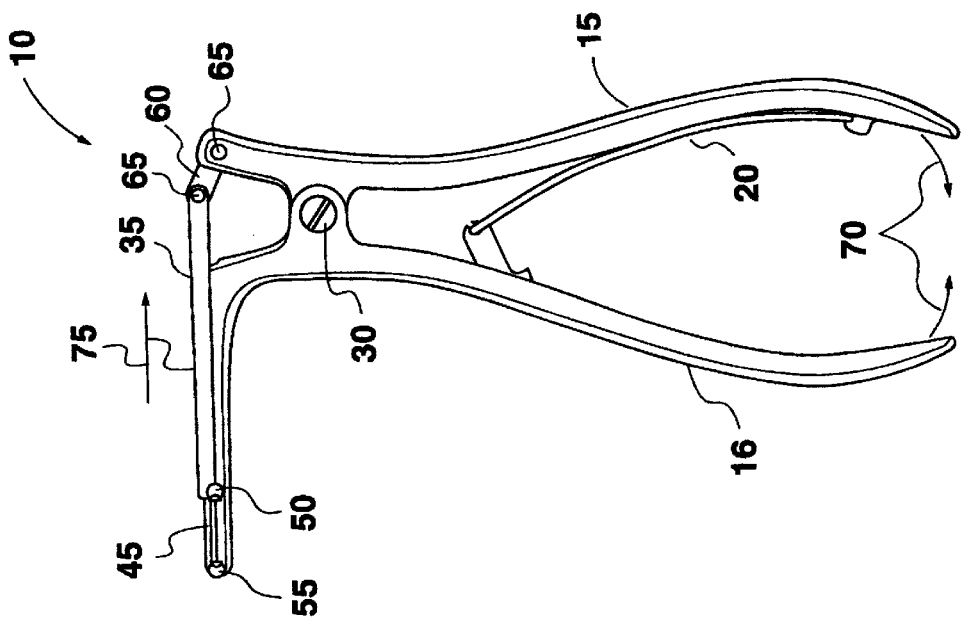
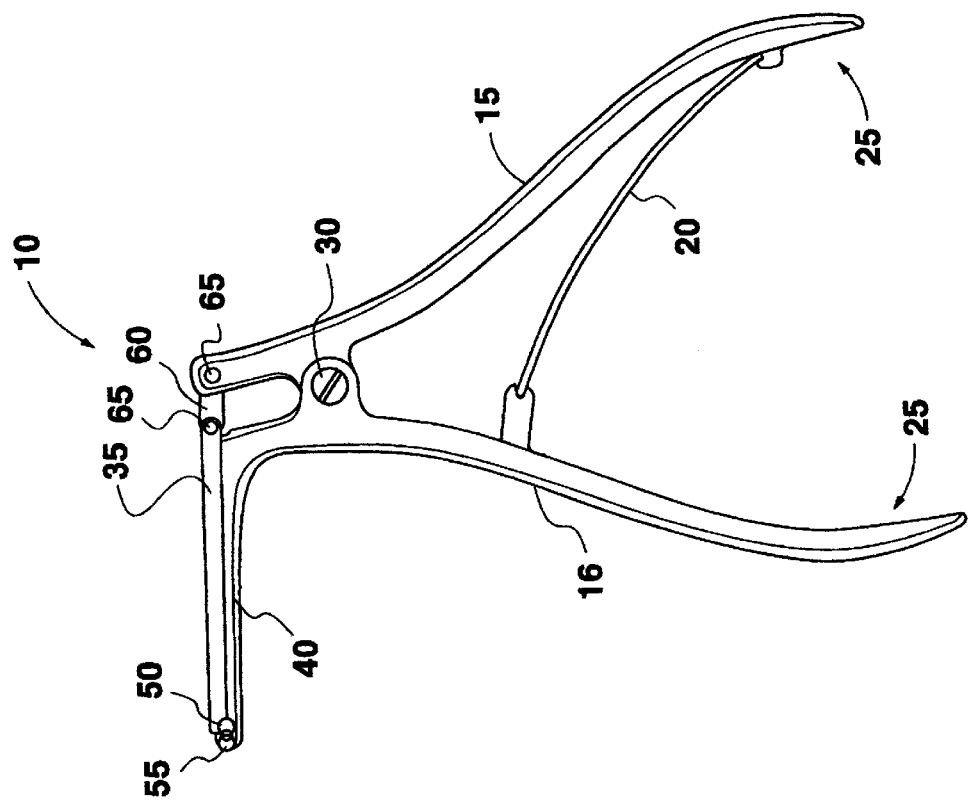

DENTIST'S MATRIX CONTACT INSTRUMENT

TECHNICAL FIELD

This invention relates to a hand-operated instrument having two opposing tines that spread apart when the device handles are squeezed. The tines are used to separate two teeth from a central tooth during certain tooth filling procedures by a dentist.

BACKGROUND OF THE INVENTION

In dental filling procedures for molars and premolars, a metal matrix band is placed around the tooth to be filled. It is desirable to slightly separate the two adjacent teeth, one in front and one behind the tooth being filled. The reason for the separation is to allow the adjacent teeth to move towards the filled tooth after the filling is completed to close up the gap. This prevents food particles from being lodged in the space between the filled tooth and adjacent teeth.

Tooth decay usually occurs interproximally where the teeth touch. This decay has to be removed to stop its progress in destroying the tooth. In order to remove the decay, the part of the tooth touching the tooth next to it is removed. This area of the tooth is the mesial (forward) or distal (back) part of the tooth in the mouth. This area has to be restored to its original contour to be able to touch the adjacent tooth. This contact with the other tooth is important to maintain the health of the periodontium (tissues surrounding the tooth). If the contact is weak or there is no contact (there is a gap), food will pack down between the teeth and create infection and soreness. The contact must also be restored to its original contour to function properly. If the contact is too high on the tooth and touches only near the marginal upper ridge, the contact is less and isn't as effective as keeping food out of the interproximal space. This instrument will help restore the proper contact down at the fullest portion of the tooth.

SUMMARY OF THE INVENTION

This invention is a dentist's matrix contact instrument that can obtain tighter contacts within a matrix band during restoration of posterior teeth using a composite resin material. A prior invention by the present inventor for a dentist's forceps, Ser. No. 09/861,115, now U.S. Pat. No. 6,345,983, disclosed a scissors-like forceps. These forceps have jaws that are perpendicular to the flat scissors handle portion of the device and therefore projected at right angles from the row of teeth that included the decayed tooth. This projection therefore prevented the forceps from engaging posterior teeth because of the limited spreading of the patient's mouth. The positioning of these forceps is seen in FIG. 1 of the U.S. Pat. No. 6,345,983.

BRIEF DESCRIPTION OF THE DRAWINGS

FIG. 1 is a front elevation of the present invention.

FIG. 2 is a front elevation of the present invention with the handles compressed.

DETAILED DESCRIPTION OF THE INVENTION

Figure 3:
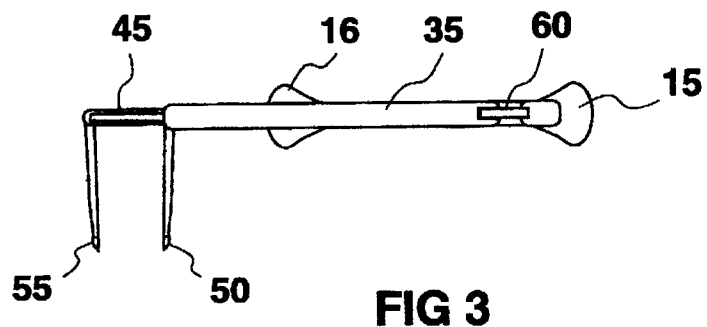
FIG. 3 is a top view of the present invention.
Figure 4:
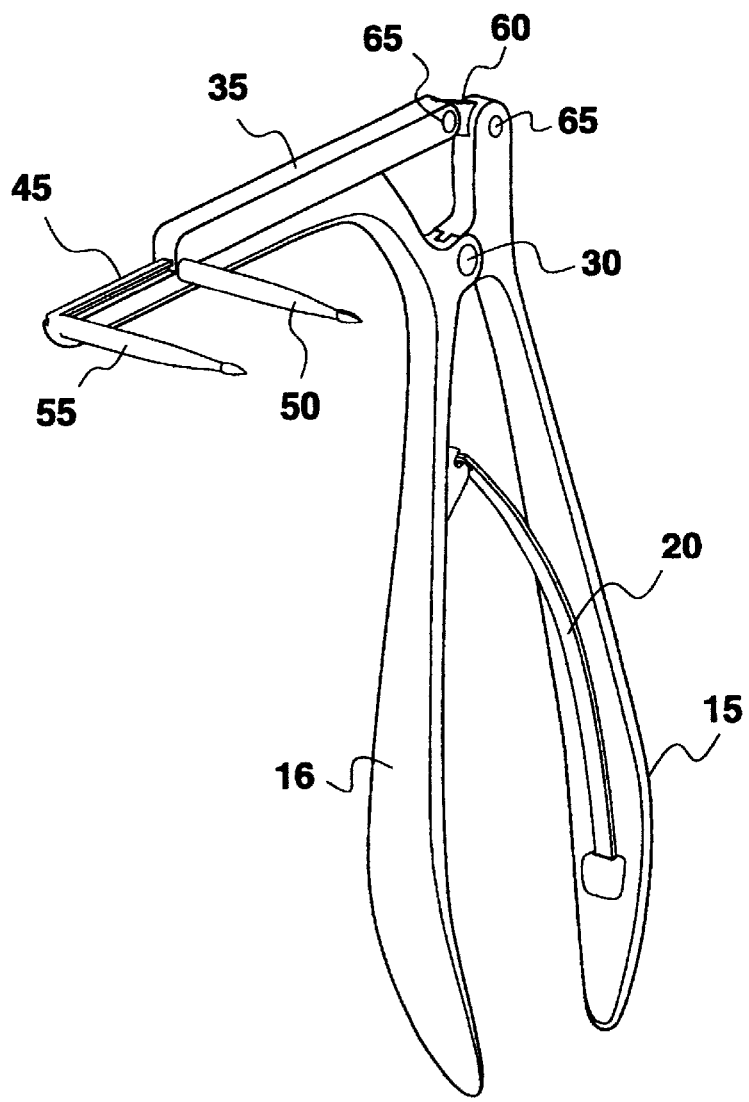
FIG. 4 is a front perspective view of the present invention.

The dentist's contact tooth separation instrument will be described by referring to FIGS. 1–5. The dentist's instrument 10 consists of a pair of handles 15 and 16, which act against spring 20 when squeezed. The position shown in FIG. 1 is the open handle position, as indicated by open arrows 25 and maintained opened by the spring 20. The handles are joined by handle pivot 30 and activate an upper movable slide 35 over the lower arm 40. The upper slide 35 is held captive against lower arm 40 by keyway 45 (FIGS. 2 and 3). A pair of tines, the mesial tine 50 and distal tine 55 are affixed perpendicular to the plane of the arm, 40, slide 35 and handles 15 and 16. The upper slide 35 connects to the top of handle 15 by connector 60 and pins 65.

FIG. 2 illustrates the instrument 10 in the activated position after compression of handles 15 and 16 in the direction of arrows 70. In this activated position the movable slide 35 is moved to the right as shown by slide arrow 75. Consequently, the tines 50 and 55 are separated by this activation and will maintain this position as long as the handles 15 and 16 are compressed. This activated position is more clearly shown in FIG. 4, and is the position that will be used to slightly spread two teeth that are adjacent to a molar being repaired by a dentist.

Figure 5:
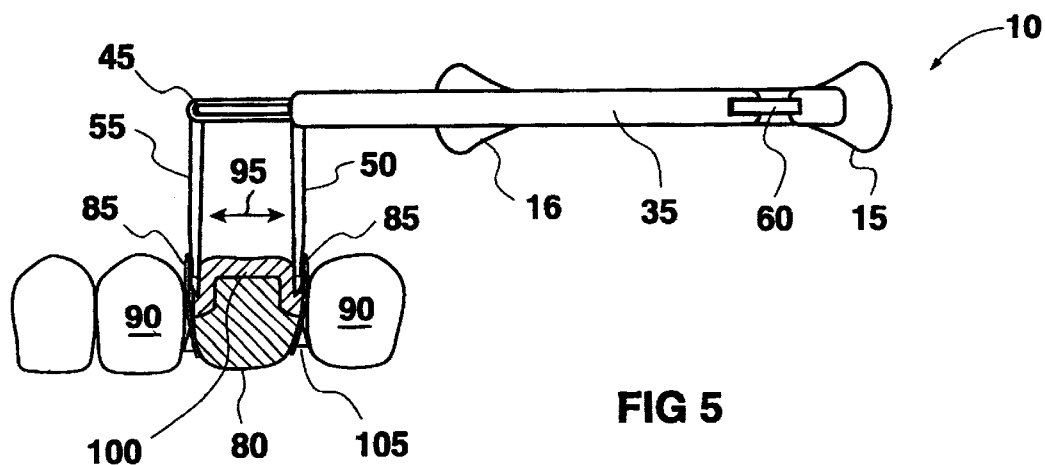
FIG. 5 is a partial section and side elevation of a row of teeth having the present invention in a horizontal position.
Figure 6:
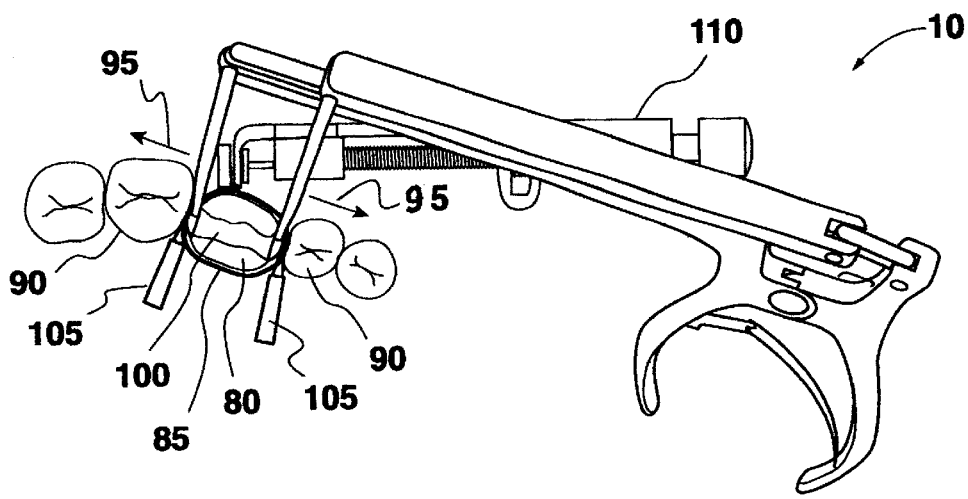
FIG. 6 is a top view of the row of teeth having the present invention rotated to a vertical position.

FIGS. 5 and 6 illustrate use of the tool by a dentist filling a molar cavity that is a posterior tooth, i.e., near the back of the mouth. In FIG. 5 the molar 80 (in cross-section) is surrounded by the metal matrix 85 (FIGS. 5 and 6) and the tool is activated to press the matrix 85 against adjacent teeth 90. This compression is shown by matrix direction arrows 95 that press and spread the adjacent teeth 90. The drilled part of the tooth is filled by a quick heat-setting resin 100 and the tool 10 is held for a short curing period in this matrix and tooth compression position. Once the matrix 85 is removed, the tooth 80 maintains proper contact with the adjacent teeth 90 after wedges 105 are removed. The matrix is removed by loosening and disengaging the matrix clamp 110. After removal of the tines 50 and 55, the aperture or footprint left behind is filled with additional resin and cured. The tooth can then be contoured and cured for a completed restoration. The tool can be used to restore contact with a single adjacent tooth or as shown with contacts to two adjacent molars. The contacts are made by the mesial (front) tine and the distal tine, which lie perpendicular to the plane of the handles. This tine orientation permits the handles to extend away from the centerline of the mouth, thereby permitting access to the molar area. A similar tool having the tines 180 degrees from that shown in FIGS. 5 and 6 permits access to molars on the opposite side of the mouth. The tines may be coated with a diamond dust to grip the matrix band more securely.

What is claimed is:

1. A dentist's tooth separator instrument comprising:
   (a) a pair of spring-loaded handles;
   (b) a lower arm attached to a first handle;
   (c) a diamond dust-coated distal tine connected at a right angle to the lower arm;

(d) an upper linear motion slide attached to the lower arm, the slide having a diamond dust-coated mesial tine connected parallel to the distal tine; and (e) a movable connector attaching the slide to a second handle wherein compression of the handles separates the distal tine from the mesial tine.

2. The instrument of claim 1 wherein the upper movable slide is attached to the lower arm by a keyway.

3. The instrument of claim 1 wherein spring-loaded handle action moves the tines to a closed position.

4. The instrument of claim 1 wherein a tine orientation perpendicular to the handles provides a handle orientation that extends away from a patient's mouth thereby permitting access to a molar tooth area.

5. The instrument of claim 1 wherein the handles are joined by a handle pivot in proximity to the movable connector and lower arm.

6. The instrument of claim 5 wherein a mechanical advantage of tine force over handle force is provided by handle lengths being larger than a length from handle pivot to connector arm.

* * * * *